US00PP35891P3

(12) United States Plant Patent
Olesen

(10) Patent No.: US PP35,891 P3
(45) Date of Patent: Jul. 2, 2024

(54) CLIMBING ROSE PLANT NAMED 'POULCY042'

(50) Latin Name: *Rosa hybrida*
Varietal Denomination: Poulcy042

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,477

(22) Filed: Sep. 8, 2023

(65) Prior Publication Data

US 2024/0107906 P1 Mar. 28, 2024

(30) Foreign Application Priority Data

Sep. 30, 2022 (QZ) ..... PBR 2022/2154

(51) Int. Cl.
*A01H 5/02* (2018.01)
*A01H 6/74* (2018.01)

(52) U.S. Cl.
USPC ..... Plt./115
CPC ..... *A01H 6/749* (2018.05)

(58) Field of Classification Search
USPC ..... Plt./101, 109, 115
See application file for complete search history.

*Primary Examiner* — Susan McCormick Ewoldt

(57) ABSTRACT

A new garden rose plant of the climbing class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulcy042'.

This application claims priority to Plant Breeder's Rights Application Number 2022/2154, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulcy042', originated as a single seedling from the stated cross. The new variety may be distinguished from its male pollen parent and female seed parent primarily by the following characteristics. The male pollen parent plant has the growth habit of a hybrid tea rose, while the new variety has the growth habit of a climbing rose. The female seed parent plant has orange-red flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulcy042' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulcy042' was selected in the spring of 2015 by the inventor as a single plant from the progeny of the aforementioned hybridization.

Asexual reproduction of 'Poulcy042' by rooted cuttings was first done by Mogens N. Olesen in the nursery in Fredensborg, Denmark in July, 2015. This initial and other subsequent asexual propagations conducted in controlled environments have demonstrated that the characteristics of 'Poulcy042' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy042'.

Specifically illustrated in FIG. 1 of the drawings are open flowers viewed from above and the side, a cluster of flowers and flower buds on the branch, flower petals detached, sepals detached showing the receptacle and reproductive flower parts.

Figure 1:
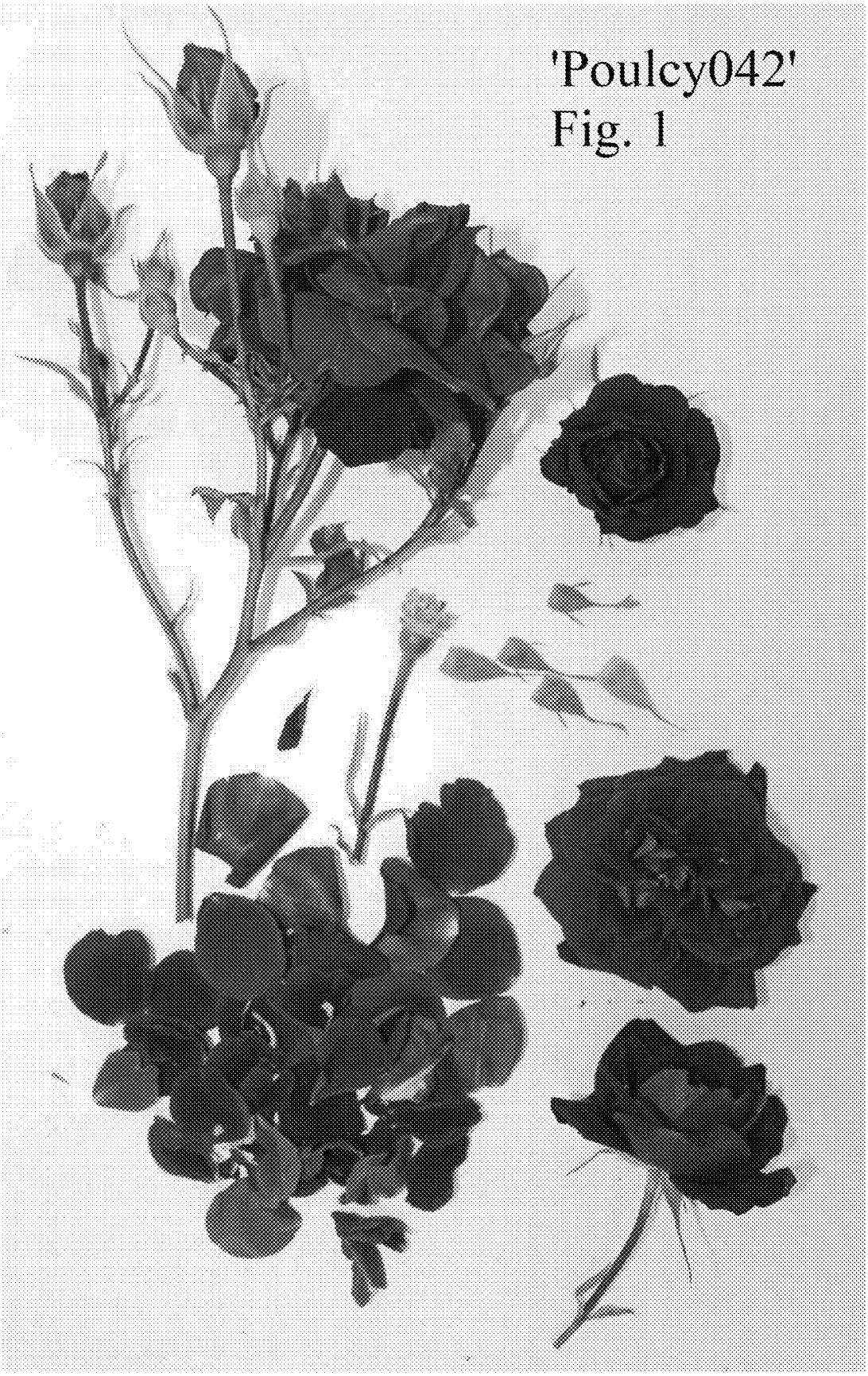
Figure 2:
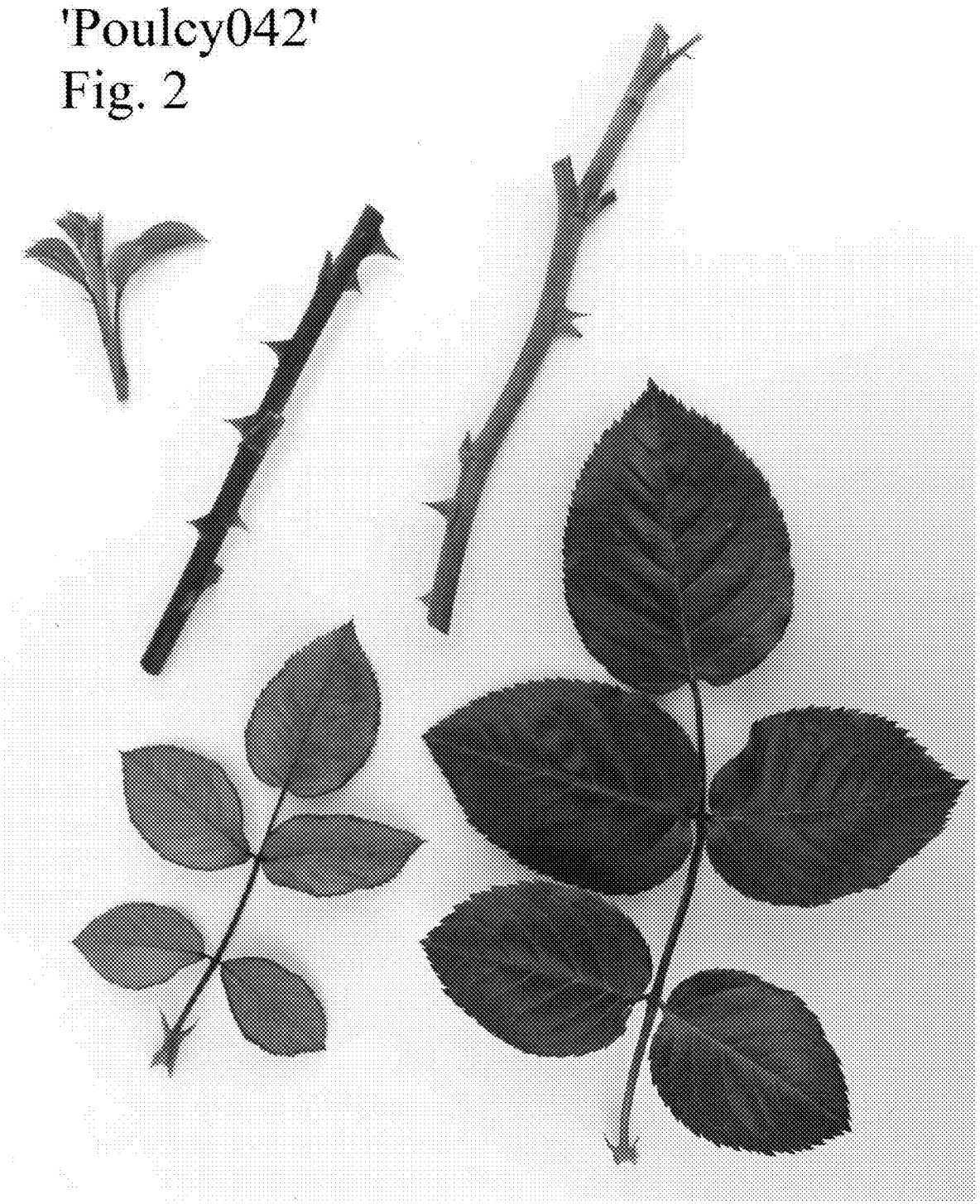

Specifically illustrated in FIG. 2 of the drawings are mature and juvenile leaves and bare stems with prickles. Plants shown are 18 months old.

DETAILED DESCRIPTION OF THE VARIETY

The following is a description of 'Poulcy042', as observed in its growth in an outdoor nursery in Odense Denmark. Observed plants are 18 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulnorm', U.S. Plant Pat. No. 12,552 are compared to the claimed plant. While 'Poulcy042' has about 61 flower petals, 'Poulnorm' has 45-50 flower petals. Open flowers of 'Poulnorm' are generally Red Group 34A in color while 'Poulcy042' has a general flower colour tonality of Red Group 46A. 'Poulnorm' forms flowers singly, or in clusters of up to 3 flower buds per stem, while the claimed plant produces 5 or more flower buds on the stem.

FLOWER AND FLOWER BUD

Blooming habit: Continuous.

Flower bud:

- *Size.*—Upon opening, 25 mm in length from base of receptacle to end of bud. Bud diameter is 16 mm.
- *Bud form.*—Urceolate.
- *Bud color.*—As sepals divide petals are Red Group 46A.
- *Sepal inner surface.*—Color: Yellow-Green Group 146D. Surface: Strongly pubescent.
- *Sepal outer surface.*—Color: Yellow-Green Group 144A with intonations of Greyed-Purple Group 185A. Texture: Smooth.
- *Sepal shape.*—Apex: Cirrhose. Base: Flat at union with receptacle.
- *Sepal margin.*—Margins have moderate or weak foliaceous appendages on three of the five sepals.
- *Sepal size.*—About 30 mm long, 11 mm wide.
- *Receptacle.*—Texture: Smooth. Size: 7 mm in height, 8 mm wide. Color: Yellow-Green Group 144A with strong intonations of Greyed-Purple Group 187B. Shape: Campanulate.
- *Pedicel.*—Surface: Rough with stipitate glands. Length: On average 50 mm. Diameter: About 3 mm. Color: Yellow-Green Group 144A with strong intonations of Greyed-Purple Group 187B. Strength: Strong.
- *Peduncle.*—Length: 30 to 80 mm. Diameter: About 3.5 mm. Color: Yellow-Green Group 144A with strong intonations of Greyed-Purple Group 187B. Texture: Somewhat rough with small prickles.

Flower bud development: Flower buds are borne in clusters of about 5 flower buds on each peduncle.

Flower bloom:

- *Fragrance.*—Moderate floral.
- *Duration.*—The blooms have a duration on the plant of approximately 18 days. Petals fall cleanly away from plant after flowers have fully matured.
- *Size.*—Flower diameter is 105 mm when open. Flower depth is 50 mm.
- *Flower shape.*—Rosette with many slightly overlapping petals of different sizes.
- *Shape of flower, side view.*—The upper portion is convex. The lower portion is deep concave.

Petalage: Under normal conditions, flowers have about 61 petals.

General tonality of flower: Open flowers are Red Group 46A. After 10 days tonality fades to Red Group 46B.

Petal color:

- *Upon opening, outer petals.*—Upper surface: Red Group 46A to 46B. Lower surface: Red Group 53A.
- *Upon opening, inner petals.*—Upper surface: Red Group 46A to 46B. Lower surface: Red Group 53A.
- *Basal petal spots, upon opening.*—Upper surface: Yellow Group 4D, small. Lower surface: Yellow Group 4D, small.
- *After opening, outer petals.*—Upper surface: Red Group 45A. Lower surface: Red Group 46A.
- *After opening, inner petals.*—Upper surface: Red Group 45A. Lower surface: Red Group 46A.
- *Basal petal spots, after opening.*—Upper surface: Yellow Group 4D, small. Lower surface: Yellow Group 4D, small.

Petals:

- *Petal reflex.*—Strong.
- *Margin.*—Entire, some petals have a cleft. Moderate undulations.
- *Shape.*—Broad and elliptic. Apex shape: Rounded. Base shape: Acute.
- *Size.*—39 mm (l)×40 mm (w).
- *Texture.*—Smooth.
- *Thickness.*—Average.

Petaloids:

- *Size.*—20 mm (l) by 12 mm (w).
- *Quantity.*—About 20.
- *Shape.*—Elliptical with an acute base and rounded apex.
- *Color.*—Underside Red Group 46A, above Red Group 45A. Petaloid spot Yellow Group 4C.

Reproductive flower parts:

- *Pollen.*—None observed.
- *Anthers.*—Size: 3 mm in length. Color: Yellow Group 8D. Quantity: 50 on average.
- *Filaments.*—Color: Yellow Group 10A and Orange-Red Group 35A. Length: 5 mm.
- *Pistils.*—Length: 5 mm. Quantity: 47 on average.
- *Stigmas.*—Color: Yellow White 158C.
- *Styles.*—Color: Green White 157A.
- *Location of stigmas.*—Inferior in location relative to the length of the filaments and the height of the anthers.
- *Hips.*—None Observed.

PLANT

Plant growth: Climbing. Plants are 120 cm in height, and 65 cm wide.

Stems:

- *Color of juvenile growth.*—Yellow-Green Group 146A with intonations of Greyed-Purple Group 183A.
- *Color of mature growth.*—Yellow-Green Group 146A.
- *Length.*—Canes are about 55 cm from the base of the plant to the flowering portion.
- *Diameter.*—About 8 mm.
- *Internodes.*—On mature canes about 45 to 73 mm between nodes.
- *Surface texture.*—Young wood: Smooth. Older wood: Smooth.

Long prickles:

- *Incidence.*—7 prickles per 10 cm of stem.
- *Size.*—Average length of prickles on mature stems is 12 mm.
- *Shape.*—Upper portion is linear. Lower portion is concave.

*Color*.—Juvenile prickles: Greyed-Purple Group 183B with intonations of Yellow-Green Group 146B. Mature prickles: Greyed-Purple Group 183C and Greyed-Orange Group 164B.

Plant foliage:

*Compound leaf*.—About 230 mm (l)×160 mm (w).

*Quantity*.—2 leaves per 10 cm of stem on average.

*Leaf bearing angle to the stem*.—90 degrees.

*Color of juvenile foliage*.—Upper side: Yellow-Green Group 146A with marginal intonations of Greyed-Purple Group 183A. Lower side: Yellow-Green Group 146B.

*Color of mature foliage*.—Upper side: Yellow-Green Group 147A. Lower side: Yellow-Green Group 147B.

Plant leaves and leaflets:

*Stipules*.—Size: 21 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 55 mm. Diameter: 2 mm. Upper surface color: Greyed-Purple Group 183A and Yellow-Green Group 146A. Lower surface color: Yellow-Green Group 144A.

*Rachis*.—Length: About 90 mm. Upper surface color: Yellow-Green Group 146B with some intonations of Greyed-Purple Group 183A. Lower surface color: Yellow-Green Group 144A.

*Leaflet*.—Quantity: Normally 5 leaflets. Margins: Serrated. Size: Terminal leaflets are about 90 mm long, 66 mm wide. Shape: Generally elliptical. Base: Rounded. Apex: Acuminate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulcy042' substantially as described and illustrated herein.

* * * * *

'Poulcy042'

'Poulcy042'